(12) United States Patent
Balganesh et al.

(10) Patent No.: US 6,476,053 B1
(45) Date of Patent: Nov. 5, 2002

(54) MYCOBACTERIAL INHIBITORS

(75) Inventors: Meenakshi Balganesh, Bangalore (IN); Kantharaj Ethirajulu, Bangalore (IN); Babita Singh Ganguly, Bangalore (IN); Ramachandran Janakiraman, Bangalore (IN); Parvinder Kaur, Bangalore (IN); Rangarao Kajipalya, Bangalore (IN); Santosh Nandan, Bangalore (IN); Ramanujulu Pondi Murugappan, Bangalore (IN); Narayanan Ramamurthy, Bangalore (IN); Balasubramanian Venkataraman, Bangalore (IN)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/331,623

(22) PCT Filed: May 3, 1999

(86) PCT No.: PCT/SE99/00732

§ 371 (c)(1),
(2), (4) Date: Jun. 22, 1999

(87) PCT Pub. No.: WO99/65483

PCT Pub. Date: Dec. 23, 1999

(30) Foreign Application Priority Data

May 5, 1998 (IN) ........................................ 969/MAS/98
Jun. 15, 1998 (SE) ............................................... 9802118

(51) Int. Cl.[7] ................................................ A61F 31/40
(52) U.S. Cl. ........................ 514/328; 514/425; 514/417
(58) Field of Search ................................ 514/328, 425, 514/417; 546/192, 209, 210; 548/473, 481, 523, 545

(56) References Cited

U.S. PATENT DOCUMENTS 3,883,342 A * 5/1975 Abramitis et al.

OTHER PUBLICATIONS

Korhalkar, et al., Indian Drugs 29: 306–307 (1982).

* cited by examiner

Primary Examiner—Joseph K. McKane
Assistant Examiner—Kamal Saeed
(74) Attorney, Agent, or Firm—White & Case LLP

(57) ABSTRACT

The invention provides the use of certain succinimide compounds in the treatment of mycobacterial diseases.

7 Claims, No Drawings

MYCOBACTERIAL INHIBITORS

This application is a 371 of PCT/SE99/00732 filed May 3, 1999.

The present invention relates to compounds for use in the treatment of mycobacterial diseases, particularly those diseases caused by pathogenic mycobacteria such as *Mycobacterium tuberculosis, M. bovis, M. avium* and *M. marinum*.

Tuberculosis is still a major public health problem affecting nearly all parts of the world. Based on skin test reactivity it has been estimated that about one-third of the world's population, i.e., 1.7 billion people, are infected with *Mycobacterium tuberculosis*. Despite the availability of effective chemotherapies, it is responsible for three million deaths and from eight to ten million new cases annually and thus remains the leading cause of death world-wide due to a single infectious agent: 26% of all preventable deaths, 7% of all deaths. According to the World Health Organisation, 450,000 deaths per year due to tuberculosis in developing countries occur in children under fifteen years of age, and the disease mostly affects the younger, more productive adults.

There are five front-line drugs known to be highly effective against *M. tuberculosis* and five second-line drugs that can be used when resistance to one or more of the front-line drugs is detected. The preferred mode of treatment for tuberculosis is the short course chemotherapy in which there are two phases. The first phase consists of a daily regimen for two months with isoniazid (300 mg), rifampicin (600 mg), pyrazinamide (3 g) and ethambutol (1.5 g). The second phase or the continuation phase consists of a daily regimen for the next four months with isoniazid and rifampicin. Although infection with drug-sensitive strains of *M. tuberculosis* can be effectively cured with the short course chemotherapy, the cure rate is very poor in most countries due to poor compliance which is reflective of the long duration of therapy.

The situation is further complicated by the rapid emergence of multi-drug resistant tuberculosis (MDR-TB) strains. For example, in certain populations, the incidence of resistance to isoniazid is as high as 26% and the resistance to rifampicin is about 15%. Prior to 1984, about 10% of tubercle bacilli isolated from patients in the United States were resistant to at least one single mycobacterial drug. By 1984, this figure had risen to 52%, of which over half (32%) were resistant to more than one drug (MDR-TB). Ten percent of the recorded MDR-TB cases have occurred in previously healthy people whose mortality rate—70 to 90%—has been nearly the same as that of immunosuppressed individuals with MDR-TB. The number of cases of MDR-TB has doubled since 1984 and in many of them the tubercle bacilli are resistant to both isoniazid and rifampicin. The median interval between diagnosis of MDR-TB and death is only four weeks and therefore MDR-TB demands a shorter response time between diagnosis and appropriate commencement of treatment. However, MDR-TB is difficult to treat as such since most patients do not respond very well to the second-line drugs and the cost of alternate treatment procedures, including hospitalisation and possibly surgery, increases the cost to as much as ten times the cost of traditional treatment.

Thus, there is an urgent medical need to identify new drugs with significant therapeutic activity against single- or multiple-drug resistant strains of *M. tuberculosis* and with pharmacokinetic properties that permit reduced dosing which will in turn encourage better compliance.

In accordance with the present invention, there is therefore provided the use of a compound of general formula

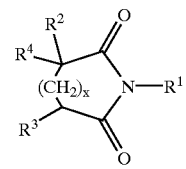

(I)

wherein x is 0 or 1;

$R^1$ represents a hydrogen atom, or a $C_1$–$C_{20}$ alkyl or myrtanyl group, or a phenyl or benzyl group optionally substituted in the aromatic ring by one or more substituents selected from amino, nitro, hydroxyl, carboxyl, halogen, trifluoromethyl, $C_1$–$C_6$ alkyl, $C_1$–$C_6$ alkoxy, $C_1$–$C_6$ alkoxycarbonyl, piperidyl, piperazinyl and morpholinyl, or a group $(CH_2)_y CONH$—$R^5$ where y is an integer from 1 to 6 and $R^5$ represents a phenyl group optionally substituted by one or more substituents selected from amino, nitro, hydroxyl, carboxyl, halogen, trifluoromethyl, $C_1$–$C_6$ alkyl, $C_1$–$C_6$ alkoxy, $C_1$–$C_6$ alkoxycarbonyl, piperidyl, piperazinyl and morpholinyl; and either $R^2$ represents a hydrogen atom or a $C_1$–$C_6$ alkyl group, or $R^2$ together with $R^3$ represents a carbon-carbon single bond provided that x is 0, or $R^2$ together with $R^4$ represents a group $=CH_2$, $R^3$ represents a hydrogen atom or is linked to $R^2$ as defined above, and $R^4$ represents a hydrogen atom or a $C_1$–$C_6$ alkyl group; or a $C_1$–$C_{10}$ alkylamino group optionally substituted by a di($C_1$–$C_6$ alkyl)amino substituent group; or an anilino group optionally substituted in the aromatic ring by one or more substituents selected from amino, nitro, hydroxyl, carboxyl, halogen, trifluoromethyl, $C_1$–$C_6$ alkyl, $C_1$–$C_6$ alkoxy, $C_1$–$C_6$ alkoxycarbonyl, piperidyl, piperazinyl and morpholinyl; or a group —$SCH_2CH_2OH$, —$SCH_2CH_2NH_2$, —$SCH_2CH_2(NH_2)CO_2H$ or —$SCH_2CH_2NHCO$—$R^6$ where $R^6$ represents a $C_1$–$C_{10}$ alkyl or $C_3$–$C_6$ cycloalkyl group, or a phenyl group optionally substituted by one or more substituents selected from amino, nitro, hydroxyl, carboxyl, halogen, trifluoromethyl, $C_1$–$C_6$ alkyl, $C_1$–$C_6$ alkoxy, $C_1$–$C_6$ alkoxycarbonyl, piperidyl, piperazinyl and morpholinyl;

or $R^4$ is linked to $R^2$ as defined above;

or $R^2$, $R^3$ and $R^4$ together represent a phenyl group;

with the provisos that:
  (i) $R^1$, $R^2$, $R^3$ and $R^4$ do not each simultaneously represent a hydrogen atom,
  (ii) when x is 0, $R^1$ represents a 4-fluorophenyl group and $R^4$ represents a hydrogen atom, then $R^2$ and $R^3$ do not together represent a carbon-carbon single bond, and
  (iii) when x is 0, $R^1$ represents a 4-fluorophenyl group and $R^2$ and $R^3$ both represent a hydrogen atom, then $R^4$ does not represent an anilino, 4-chloroanilino, 2,6-dichloroanilino, 3,4-dichloroanilino, 2,5-dichloroanilino, 3-chloro-4-fluoroanilino or 4-fluoroanilino group;

or a pharmaceutically acceptable salt or solvate thereof, in the manufacture of a medicament for use in the treatment of a mycobacterial disease, in particular tuberculosis.

In the context of the present specification, unless otherwise stated, an alkyl (substituent) group or an alkyl moiety in an alkoxy or alkoxycarbonyl substituent group may be linear or branched.

Preferably $R^1$ in formula (I) represents a hydrogen atom, or a $C_1$–$C_{15}$, more preferably $C_1$–$C_{10}$, alkyl or myrtanyl group, or a phenyl or benzyl group optionally substituted in the aromatic ring by one to four, particularly one or two, substituents selected from amino, nitro, hydroxyl, carboxyl, halogen (e.g. fluorine, chlorine or bromine), trifluoromethyl, $C_1$–$C_4$ alkyl (e.g. methyl, ethyl, propyl, isopropyl or butyl), $C_1$–$C_4$ alkoxy (e.g. methoxy, ethoxy, propoxy, or butoxy), $C_1$–$C_4$ alkoxycarbonyl (e.g. methoxycarbonyl, ethoxycarbonyl, propoxycarbonyl or butoxycarbonyl), piperidyl, piperazinyl and morpholinyl, or a group $(CH_2)_y$CONH—$R^5$ where y is an integer 1, 2, 3 or 4 and $R^5$ represents a phenyl group optionally substituted by one to four, particularly one or two, substituents selected from amino, nitro, hydroxyl, carboxyl, halogen (e.g. fluorine, chlorine or bromine), trifluoromethyl, $C_1$–$C_4$ alkyl (e.g. methyl, ethyl, propyl, isopropyl or butyl), $C_1$–$C_4$ alkoxy (e.g. methoxy, ethoxy, propoxy, or butoxy), $C_1$–$C_4$ alkoxycarbonyl (e.g. methoxycarbonyl, ethoxycarbonyl, propoxycarbonyl or butoxycarbonyl), piperidyl, piperazinyl and morpholinyl.

The group $R^1$ especially represents a hydrogen atom, or a $C_4$–$C_{10}$ alkyl (e.g. butyl, pentyl, hexyl, heptyl, octyl, nonyl or decyl) or myrtanyl group, or a phenyl group substituted by a piperidyl substituent group, or a group $(CH_2)_y$CONH—$R^5$ where y is 1 or 2 and $R^5$ represents a phenyl group substituted by a piperidyl substituent group.

Preferably $R^2$ represents a hydrogen atom or a $C_1$–$C_4$ alkyl, particularly methyl, group, or $R^2$ together with $R^3$ represents a carbon-carbon single bond provided that x is 0, or $R^2$ together with $R^4$ represents a group =$CH_2$.

$R^4$ preferably represents a hydrogen atom or a $C_1$–$C_4$ alkyl group (e.g. methyl, ethyl, propyl or butyl); or a $C_2$–$C_{10}$ alkylamino group optionally substituted by a di($C_1$–$C_6$ alkyl)amino, especially di($C_1$–$C_4$ alkyl)amino, substituent group; or an anilino group optionally substituted in the aromatic ring by one to four, particularly one or two, substituents selected from amino, nitro, hydroxyl, carboxyl, halogen (e.g. fluorine, chlorine or bromine), trifluoromethyl, $C_1$–$C_4$ alkyl (e.g. methyl, ethyl, propyl, isopropyl or butyl), $C_1$–$C_4$ alkoxy (e.g. methoxy, ethoxy, propoxy, or butoxy), $C_1$–$C_4$ alkoxycarbonyl (e.g. methoxycarbonyl, ethoxycarbonyl, propoxycarbonyl or butoxycarbonyl), piperidyl, piperazinyl and morpholinyl; or a group —$SCH_2CH_2OH$, —$SCH_2CH_2NH_2$, —$SCH_2CH_2(NH_2)CO_2H$ or —$SCH_2CH_2NHCO$—$R^6$ where $R^6$ represents a $C_5$–$C_{10}$ alkyl or $C_3$–$C_6$ cycloalkyl group, or a phenyl group optionally substituted by one or more substituents selected from amino, nitro, hydroxyl, carboxyl, halogen (e.g. fluorine, chlorine or bromine), trifluoromethyl, $C_1$–$C_4$ alkyl (e.g. methyl, ethyl, propyl, isopropyl or butyl), $C_3$–$C_6$ alkoxy (e.g. propoxy, butoxy, pentoxy or hexyloxy), $C_1$–$C_4$ alkoxycarbonyl (e.g. methoxycarbonyl, ethoxycarbonyl, propoxycarbonyl or butoxycarbonyl), piperidyl, piperazinyl and morpholinyl; or $R^4$ is linked to $R^2$ as defined above.

It is preferred that $R^4$ represents a hydrogen atom, a methyl or ethyl group, a $C_2$–$C_{10}$ alkylamino group optionally substituted by a di($C_2$–$C_4$ alkyl)amino substituent group, an anilino group substituted by a piperidyl substituent group, —$SCH_2CH_2OH$, —$SCH_2CH_2NH_2$, —$SCH_2CH_2(NH_2)CO_2H$, —$SCH_2CH_2NHCO$—$R^6$ where $R^6$ represents a $C_7$ alkyl, cyclopropyl, cyclopentyl or cyclohexyl group or a phenyl group substituted by a nitro, $C_1$–$C_4$ alkyl or $C_3$–$C_6$ alkoxy substituent group, or $R^4$ is linked to $R^2$ as defined above.

Particularly preferred compounds of formula (I) include:

1-Decylpyrrolidine-2,5-dione,
1-Nonylpiperidine-2,6-dione,
2-((6,6-Dimethylbicyclo[3,1,1]hept-2-yl)methyl)isoindole-1,3-dione,
1-((6,6-Dimethylbicyclo[3,1,1]hept-3-yl)methyl)-3-methyl-3-pyrroline-2,5-dione,
3-Methyl-1-nonyl-3-pyrroline-2,5-dione,
3-Methylene-1-nonylpyrrolidine-2,5-dione,
3-Methyl-1-octyl-3-pyrroline-2,5-dione,
3-Methylene-1-octylpyrrolidine-2,5-dione,
(4-(3-methyl-2,5-dioxo-3-pyrrolinyl)phenyl)piperidine,
1-Octyl-3-pyrroline-2,5-dione,
1-Decyl-3-pyrroline-2,5-dione,
1-Nonyl-3-pyrroline-2,5-dione,
1-Butyl-3-pyrroline-2,5-dione,
1-Hexyl-3-pyrroline-2,5-dione,
1-(4-Piperidylphenyl)-3-pyrroline-2,5-dione,
1-(Octyl-3-(octylamnino)-pyrrolidine-2,5-dione,
1-Decyl-3-(decylamino)pyrrolidine-2,5-dione,
3-(Octylamiino)-3-pyrrolidine-2,5-dione,
3-(Heptylamino)-1-nonyl pyrrolidine-2,5-dione,
1-Nonyl-3-(nonylamino)pyrrolidine-2,5-dione,
1-Nonyl-3-(octylamino)pyrrolidine-2,5-dione,
2-Arnino-3-(3-methyl-1-nonyl-2,5-dioxo-pyrrolidin-3-ylthio)propanoic acid,
2-Amnino-3-(3-methyl-1-octyl-2,5-dioxo-pyrrolidin-3-ylthio)propanoic acid,
2-Amino-3-(1-octyl-2,5-dioxo-pyrrolidin-3-ylthio)propanoic acid,
3-Methyl-1-octylpyrrolidine-2,5-dione,
3-Methyl-1-nonylpyrrolidine-2,5-dione,
2-(2,5-Dioxopyrrolidinyl)-N-(4-piperidylphenyl)ethanamiide,
2-(2,5-Dioxopyrrolidinyl)-N-(4-piperidylphenyl)propanacide,
3-Ethyl-1-nonylpyrrolidine-2,5-dione,
3-(2-Aminoethylthio)-1-nonylpyrrolidine-2,5-dione,
2-Ethyl-N-(2-(1-nonyl-2,5-dioxopyrrolidin-3-ylthio)ethyl)hexanamide,
Cyclopropyl-N-(2-(1-nonyl-2,5-dioxopyrrolidin-3-ylthio)ethyl)formamide,
(4-Butylphenyl)-N-(2-(1-nonyl-2,5-dioxopyrrolidin-3-ylthio)ethyl)formamide,
(4-Hexyloxyphenyl)-N-(2-(1-nonyl-2,5-dioxopyrrolidin-3-ylthio)ethyl)formamide,
(4-Methylphenyl)-N-(2-(1-nonyl-2,5-dioxopyrrolidin-3-ylthio)ethyl)formamide,
(4-(tert-Butyl)phenyl-N-(2-(1-nonyl-2,5-dioxopyrrolidin-3-ylthio)ethyl)formamide,
Cyclopentyl-N-(2-(1-nonyl-2,5-dioxopyrrolidin-3-ylthio)ethyl)formamide, ethane,
Cyclohexyl-N-(2-(1-nonyl-2,5-dioxopyrrolidin-3-ylthio)ethyl)formamide,
(4-Nitrophenyl)-N-(2-(1-nonyl-2,5-dioxopyrrolidin-3-ylthio)ethyl)formamide,
3-((2-(Dibutylamino)ethyl)amino)-1-nonylpyrrolidine-2,5-dione,
3-((2-(Diethylamino)ethyl)amino)-1-nonylpyrrolidine-2,5-dione, 1-Nonyl-3-((4-piperidinylphenyl)amino)pyrrolidine-2,5-dione, 3-(Hydroxyethylthio)-3-methyl-1-nonylpyrrolidine-2,5-dione, 3-(2-Aminoethylthio)-3-methyl-1-nonylpyrrolidine-2,5-dione, and 3-Methyl-1-octyl-3-(octylamino)pyrrolidine-2,5-dione.

The compounds of formula (I) are known compounds or may be prepared using techniques conventional in the art. The compounds of formula (I) may, if desired, be converted to a pharmaceutically-acceptable salt or solvate thereof, preferably an acid addition salt such as a hydrochloride, hydrobromide, phosphate, acetate, fumarate, maleate, tartrate, citrate, oxalate, methanesulphonate or p-toluenesulphonate, or an alkali metal salt such as a sodium or potassium salt.

Certain compounds of formula (I) are capable of existing in stereoisomeric forms. It will be understood that the invention encompasses all geometric and optical isomers of the compounds of formula (I) and mixtures thereof including racemates. Tautomers and mixtures thereof also form an aspect of the present invention.

The compounds of formula (I) are advantageous in that they possess bactericidal activity against mycobacteria, particularly pathogenic mycobacteria such as *Mycobacterium tuberculosis, M. bovis, M. aviur and M. marinum.*

Accordingly, in another aspect, the invention provides a method of treating a patient suffering from, or at risk of, a mycobacterial disease, which comprises administering to the patient a therapeutically effective amount of a compound of formula (I), or a pharmaceutically-acceptable salt or solvate thereof, as defined above.

The compounds of formula (I) and pharmaceutically-acceptable salts and solvates thereof may be used on their own but will generally be administered in the form of a pharmaceutical composition in which the formula (I) compound/salt/solvate (active ingredient) is in association with a pharmaceutically-acceptable adjuvant, diluent or carrier. Depending on the mode of administration, the pharmaceutical composition will preferably comprise from 0.05 to 99%w (percent by weight), more preferably from 0.10 to 70%w, of active ingredient, and, from 1 to 99.95%w, more preferably from 30 to 99.90%w, of a pharmaceutically-acceptable adjuvant, diluent or carrier, all percentages by weight being is based on total composition. The pharmaceutical composition may additionally contain another anti-tubercular agent and/or various other ingredients known in the art, for example, a lubricant, stabilising agent, buffering agent, emulsifying agent, viscosity-regulating agent, surfactant, preservative, flavouring or colorant.

The daily dosage of formula (I) compound administered will, of course, vary with the compound employed, the mode of administration, the treatment desired and the mycobacterial disease indicated. However, in general, satisfactory results will be obtained when the compound of formula (I) is administered at a daily dosage not exceeding 1 g, e.g. in the range from 10 to 50 mg/kg body weight.

The compounds of formula (I) may be administered systemically, e.g. by oral administration in the form of tablets, capsules, syrups, powders or granules, or by parenteral administration in the form of solutions or suspensions.

The present invention will now be further explained with reference to the following illustrative examples.

EXAMPLE 1

1-Decylpyrrolidine-2,5-dione

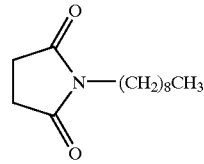

Succinimide (0.1 M) dissolved in dry dimethylformamide was treated with sodium hydride (0.1 M) at a temperature of 0° C. Nonyl bromide (0.1 M) was then added and the reaction mixture was stirred at room temperature for three hours. The reaction mixture was concentrated in vacuo and the residue extracted into ethyl acetate. The ethyl acetate layer was washed with water, dried over sodium sulphate and concentrated in vacuo. The residue obtained was chromatographed over silica gel to afford the desired product.
$^1$HNMR: δ 0.75 (3H, t), 1.10–1.20 (12H, m), 1.35–1.45 (2H, m), 2.55 (4H, s), 3.35 (2H, dd)

EXAMPLE 2

1-Nonylpiperidine-2,6-dione

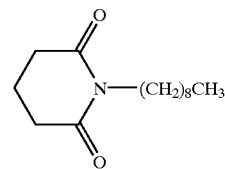

The procedure of Example 1 was repeated except that glutarimide replaced the succinimide.
$^1$HNMR: δ 0.9 (3H, t), 1.2–1.3 (12H, m), 1.4–1.5 (2H, m), 1.9 (2H, p), 2.6 (4H, t) 3.7 (2H, dd)

EXAMPLE 3

2-((6,6-Dimethylbicyclo[3,1,1,]hept-2-yl)methyl)isoindole-1,3-dione

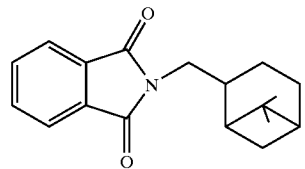

A solution of phthalic anhydride (0.1 M) in pyridine (20 ml)was treated with (−)-cis-myrtanylamine (0.1 M). The reaction mixture was heated to 90° C. for six hours. The reaction mixture was then concentrated in vacuo and the residue was extracted into ethyl acetate. The ethyl acetate layer was washed with water and with cold aqueous hydrochloric acid, then dried over sodium sulphate and finally concentrated in vacuo. The residue obtained was chromatographed over silica gel to afford the desired product.
$^1$HNMR: δ 0.85 (1H, d), 1.2 (6H, d), 1.5–1.65 (2H, m), 1.80–2.05 (4H, m), 2.27–2.35 (1H, m), 2.45–2.60 (1H, m), 3.60–3.75 (2H, m), 7.65–7.70 (2H, m), 7.78–7.85 (2H, m)

EXAMPLE 4

1-((6,6-Dimethylbicyclo[3,1,1]hept-3-yl)methyl)-3-mehtyl-3-pyrroline-2,5-dione

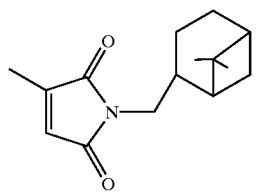

A solution of citraconic anhydride (0.1 M) in pyridine (20 ml) was treated with (−)-cis-myrtanylamine (0.1 M). The reaction mixture was heated to 90° C. for six hours. The reaction mixture was then concentrated in vacuo and the residue was extracted into ethyl acetate. The ethyl acetate layer was washed with water and with cold aqueous hydrochloric acid, then dried over sodium sulphate and finally concentrated in vacuo. The residue obtained was chromatographed over silica gel to afford the desired product.
$^1$HNMR: δ 0.65(1H, d), 1.0 (6H, d), 1.25–1.37 (1H, m), 1.55–1.80 (5H, m), 1.9 (3H, s) 2.08–2.25 (2H, m), 3.15–3.40 (2H, m), 6.1 (1H, s)

EXAMPLE 5

3-Methyl-1-nonyl-3-pyrroline-2,5-dione

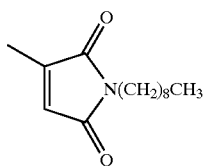

A solution of citraconic anhydride (0.1 M) in pyridine (20 ml) was treated with nonylamine (0.1 M). The reaction mixture was heated to 90° C. for six hours. The reaction mixture was then concentrated in vacuo and the residue was extracted into ethyl acetate. The ethyl acetate layer was washed with water and with cold aqueous hydrochloric acid, then dried over sodium sulphate and finally concentrated in vacuo. The residue obtained was chromatographed over silica gel to afford the desired product.
$^1$HNMR: δ 0.8 (3H, t), 1.15–1.30 (12H, m), 1.4–1.55 (2H, m), 2.05 (3H, s), 3.4 (2H, dd), 6.25 (1H, s)

EXAMPLE 6

3-Methylene-1-nonylpyrrolidine-2,5-dione

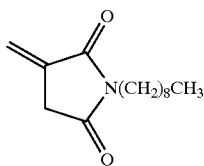

A solution of itaconic anhydride (0.1 M) in pyridine (20 ml) was treated with nonylamine (0.1 M). The reaction mixture was heated to 90° C. for six hours. The reaction mixture was then concentrated in vacuo and the residue was extracted into ethyl acetate. The ethyl acetate layer was washed with water and with cold aqueous hydrochloric acid, then dried over sodium sulphate and finally concentrated in vacuo. The residue obtained was chromatographed over silica gel to afford the desired product.

EXAMPLE 7

3-Methyl-1-octyl-3-pyrroline-2,5-dione

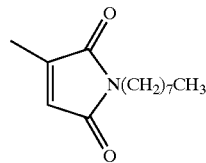

A solution of citraconic anhydride (0.1 M) in pyridine (20 ml) was treated with octylamine (0.1 M). The reaction mixture was heated to 90° C. for six hours. The reaction mixture was then concentrated in vacuo and the residue was extracted into ethyl acetate. The ethyl acetate layer was washed with water and with cold aqueous hydrochloric acid, then dried over sodium sulphate and finally concentrated in vacuo. The residue obtained was chromatographed over silica gel to afford the desired product.
$^1$HNMR: δ 0.85 (3H, t), 1.15–1.30 (12H, m), 1.45–1.60 (2H, m), 2.05 (2H, s), 3.45 (2H, dd), 6.27 (1H, s)

EXAMPLE 8

3-Methylene-1-octylpyrrolidine-2,5-dione

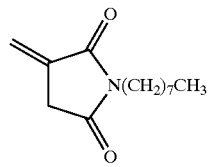

A solution of itaconic anhydride (0.1 M) in pyridine (20 ml) was treated with octylamine (0.1 M). The reaction mixture was heated to 90° C. for six hours. The reaction mixture was then concentrated in vacuo and the residue was extracted into ethyl acetate. The ethyl acetate layer was washed with water and with cold aqueous hydrochloric acid, then dried over sodium sulphate and finally concentrated in vacuo. The residue obtained was chromatographed over silica gel to afford the desired product.
$^1$HNMR: δ 0.85 (3H, t), 1.20–1.35 (10H, m), 1.50–1.65 (2H, m), 3.3 (2H, s), 5.6 (1H, s), 6.35 (1H, s)

EXAMPLE 9

(4-(3-methyl-2,5-dioxo-3-pyrrolinyl)phenyl) piperidine

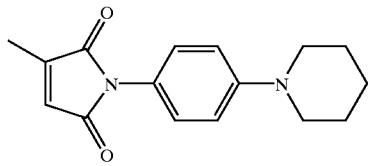

A solution of citraconic anhydride (0.1 M) in pyridine (20 ml) was treated with 4-(1-piperidyl)aniline (0.1 M). The reaction mixture was heated to 90° C. for six hours. The reaction mixture was then concentrated in vacuo and the residue was extracted into ethyl acetate. The ethyl acetate layer was washed with water and with cold aqueous hydrochloric acid, then dried over sodium sulphate and finally concentrated in vacuo. The residue obtained was chromatographed over silica gel to afford the desired product.

$^1$HNMR: δ 1.5–1.75 (6H, m), 2.12 (3H, s), 3.18 (4H, t), 6.4 (1H, br s), 6.95 (2H, d), 7.1 (2H, d)

EXAMPLE 10

1-Octyl-3-pyrroline-2,5-dione

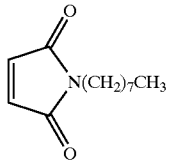

To a solution of maleic anhydride (0.1 M) in acetone (150 ml), maintained at 0° C., was added octylamine (0.1 M) dropwise over a 15 minute period. The reaction mixture was stirred for an additional period of one hour, and the white crystalline N-octyl maleimic acid that separated was filtered and dried.

A mixture of N-octyl maleimic acid (0.1 M) and sodium acetate (0.1 M) in acetic anhydride (150 ml) was heated on a steam bath for two hours. The acetic anhydride was removed under vacuum and the residual liquid product was taken up in ethyl acetate, washed with water, dried with sodium sulfate and concentrated to give a viscous liquid. Purification by flash chromatography (10% ethyl acetate in petroleum ether) yielded the desired product.

$^1$HNMR: δ 0.82 (3H, t), 1.15–1.4 (10H, m), 1.48–1.6 (2H, m), 3.45 (2H, dd), 6.65 (2H, s)

EXAMPLE 11

1-Decyl-3-pyrroline-2,5-dione

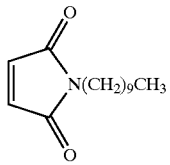

The procedure of Example 10 was repeated using decylamine in place of octylamine.

$^1$HNMR: δ 0.85 (3H, t), 1.15–1.30 (14H, m), 1.50–1.60 (2H, m), 3.47 (2H, dd), 6.65 (2H, s)

EXAMPLE 12

1-Nonyl-3-pyrroline-2,5-dione

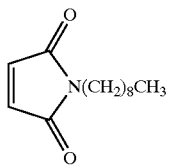

The procedure of Example 10 was repeated using nonylamine in place of octylamine.

$^1$HNMR: δ 0.85 (3H, t), 1.15–1.35 (12H, m), 1.5–1.6 (2H, m), 3.45 (2H, t), 6.65 (1H, s)

EXAMPLE 13

1-Butyl-3-pyrroline-2,5-dione

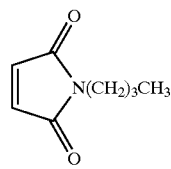

The procedure of Example 10 was repeated using butylamine in place of octylamine.

$^1$HNMR: δ 0.9 (3H, t), 1.25 (2H, m), 1.6 (2H, m), 3.5 (2H, dd), 6.65 (2H, s)

EXAMPLE 14

1-Hexyl-3-pyrroline-2,5-dione

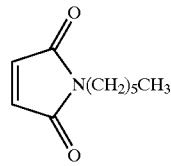

The procedure of Example 10 was repeated using hexylamine in place of octylarnine.

$^1$HNMR: δ 0.85 (3H, t), 1.2–1.35 (6H, m), 1.45–1.60 (2H, m), 3.45 (2H, dd), 6,65 (2H, s)

EXAMPLE 15

1-(4-Piperidylphenyl)-3-pyrroline-2,5-dione

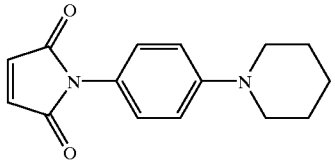

The procedure of Example 10 was repeated using 4-(piperidyl)aniline in place of octylamine.

$^1$HNMR: δ 1.5–1.65 (6H, m), 3.0–3.12 (4H, m), 6.80 (2H, s), 6.95 (2H, d), 7.1 (2H, d)

EXAMPLE 16

1-(Octyl-3-(octylamino)-pyrrolidine-2,5-dione

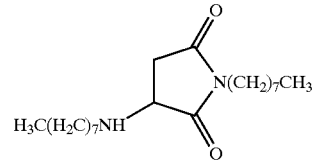

A mixture of N-octyl maleimide (0.01 M) prepared as described in Example 10 above, octylamine (0.01 M), triethylamine [catalytic, 0.1 equivalent] in acetonitrile (25 ml) was stirred for 24 hours at room temperature. Acetonitrile was removed under vacuum to leave a residual liquid product which was flash chromatographed (25% ethyl acetate in petroleum ether) to yield a white solid as the desired product.

$^1$HNMR: δ 0.8 (6H, t), 1.15–1.35 (20H, m), 1.45–1.65 (4H, m), 1.7 (1H, s), 2.45–2.65 (3H, m), 2.88 (1H, dd), 3.25 (2H, dd), 3.7 (1H, dd)

EXAMPLE 17

1-Decyl-3-(decylamino)pyrrolidine-2,5-dione

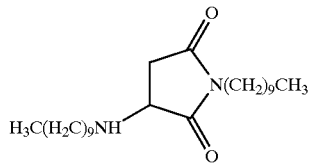

A mixture of N-decyl maleimide (0.01 M) prepared as described in Example 11 above, decylamine (0.01 M), triethylamine [catalytic, 0.1 equivalent] in acetonitrile (25 ml) was stirred for 24 hours at room temperature. Acetonitrile was removed under vacuum to leave a residual liquid product which was flash chromatographed (25% ethyl acetate in petroleum ether) to yield a white solid as the desired product.

$^1$HNMR: δ 0.8 (6H, t), 1.15–1.35 (24H, m), 1.45–1.65 (4H, m), 1.7 (1H, s), 2.45–2.65 (3H, m), 2.88 (1H, dd), 3.25 (2H, dd), 3.71 (1H, dd)

EXAMPLE 18

3-(Octylamnino)-3-pyrrolidine-2,5-dione

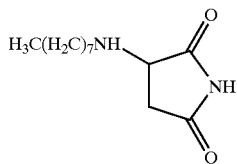

A mixture of maleimide (0.01 M), octylamine (0.01 M), triethylamine [catalytic, 0.1 equivalent] in acetonitrile (25 ml) was stirred for 24 hours at room temperature. Acetonitrile was removed under vacuum to leave a residual liquid product which was flash chromatographed (25% ethyl acetate in petroleum ether) to yield a white solid as the desired product.

$^1$HNMR: δ 0.85 (3H, t), 1.15–1.35 (1OH, m), 1.42–1.55 (2H, m), 2.50–2.70 (3H, m), 2.90 (1H, dd), 2.80 (1H, dd)

EXAMPLE 19

3-(Heptylamino)-1-nonylpyrrolidine-2,5-dione

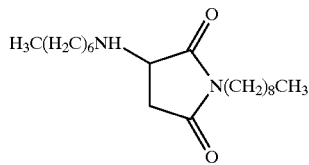

A mixture of N-nonyl maleimide (0.01 M) prepared as described in Example 12 above, heptylamine (0.01 M), triethylamine [catalytic, 0.1 equivalent] in acetonitrile (25 ml) was stirred for 24 hours at room temperature. Acetonitrile was removed under vacuum to leave a residual liquid product which was flash chromatographed (25% ethyl acetate in petroleum ether) to yield a white solid as the desired product.

EXAMPLE 20

1-Nonyl-3-(nonylamino)pyrrolidine-2,5-dione

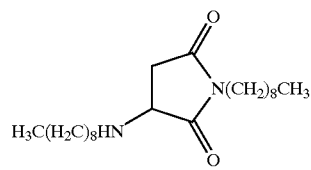

A mixture of N-nonyl maleimide (0.01 M) prepared as described in Example 12 above, nonylamine (0.01 M), triethylamine [catalytic, 0.1 equivalent] in acetonitrile (25 ml) was stirred for 24 hours at room temperature. Acetonitrile was removed under vacuum to leave a residual liquid product which was flash chromatographed (25% ethyl acetate in petroleum ether) to yield a white solid as the desired product.

$^1$HNMR: δ 0.85 (6H, t), 1.15–1.38 (24H, m), 1.40–1.55 (4H, m), 1.70 (1H, br s), 2.45–2.70 (3H, m), 2.85 (1H, dd), 3.45 (2H, dd), 3.70 (1H, dd)

EXAMPLE 21

1-Nonyl-3-(octylamino)pyrroidine-2,5-dione

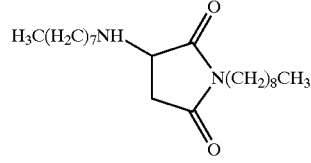

A mixture of N-nonyl maleimide (0.01 M) prepared as described in Example 12 above, octylamine (0.01 M), triethylamine [catalytic, 0.1 equivalent] in acetonitrile (25 ml) was stirred for 24 hours at room temperature. Acetonitrile was removed under vacuum to leave a residual liquid product which was flash chromatographed (25% ethyl acetate in petroleum ether) to yield a white solid as the desired product.

$^1$HNMR: δ 0.8–0.9 (6H, m), 1.18–1.30 (20H, m), 1.35–1.60 (4H, m), 2.5–2.6 (3H, m), 15 2.7–3.0 (5H, m), 3.45 (2H, dd)

EXAMPLE 22

2-Amino-3-(3-methyl-1-nonyl-2,5-dioxo-pyrrolidin-3-ylthio)propanoic acid

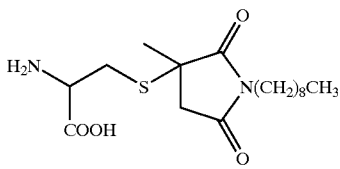

DL-Cysteine (0.0067 M) was dissolved in potassium acetate (50 mM) and the solution obtained was added slowly to N-nonyl itaconimide (0.004 M) prepared as described in Example 6 above. The reaction mixture was then dissolved in dimethylformamide with gentle stirring and triethylamine was added. Stirring was continued for a further four hours at room temperature. The progress of the reaction was monitored by reverse phase thin layer chromatography using 75% methanol in water system. The formation of the desired product was detected by the ninhydrin reaction.

EXAMPLE 23

2-Amino-3-(3-methyl-1-octyl-2,5-dioxo-pyrrolidin-3-ylthio)propanoic acid

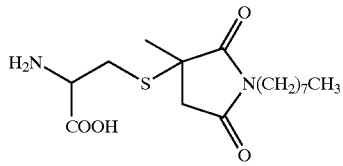

The procedure according to Example 22 was repeated using the imide of Example 8 above.

$^1$HNMR: δ 0.85 (3H, t), 1.15–1.32 (10H, m), 1.3 (3H, d), 1.4–1.52 (2H, m), 2.65–2.85 (2H, m), 3.00–3.30 (2H, m), 3.42 (2H, t), 3.85 (1H, dd)

EXAMPLE 24

2-Amino-3-(1-octyl-2,5-dioxo-pyrrolidin-3-ylthio)propanoic acid

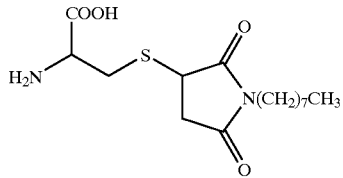

The procedure according to Example 22 was repeated using the imide of Example 10 above.

EXAMPLE 25

3-Methyl-1-octylpyrrolidine-2,5-dione

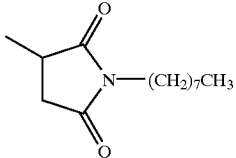

10% Palladium on carbon catalyst (5 wt %) was added to a stirred solution of N-nonyl citraconimide (0.02 M) prepared as described in Example 5 above in methanol (100 ml). Hydrogen gas was bubbled through this solution for three hours. The solution was then filtered over celite and concentrated in vacuo. Chromatography over silica gel gave the desired product.

$^1$HNMR: δ 0.85 (3H, t), 1.15–1.3 (10H, m), 1.3 (3H, d), 1.47–1.60 (2H, m), 2.28 (1H dd), 2.77–2.95 (2H, m), 3.45 (2H, dd)

EXAMPLE 26

3-Methyl-1-nonylpyrrolidine-2,5-dione

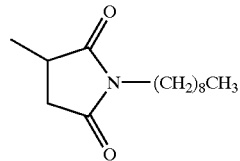

The procedure of Example 25 was repeated using instead N-octyl citraconimide prepared as described in Example 7 above.

$^1$HNMR: δ 0.85 (3H, t), 1.15–1.3 (12H, m), 1.3 (3H, d), 1.47–1.60 (2H, m), 3.45 (2H, dd) 2.77–2.95 (2H, m), 3.45 (2H, dd)

EXAMPLE 27

2-(2,5-Dioxopyrrolidinyl)-N-(4-piperidylphenyl)ethanamide

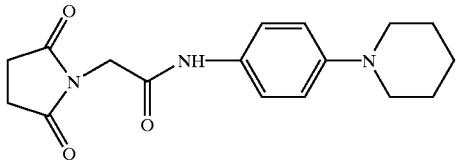

A solution of glycine benzyl ester hydrochloride (0.1 mM) in diethyl ether was treated with triethylamine (0.11 mM) and then with succinic anhydride (0.11 mM). The reaction mixture was stirred at room temperature for two hours and then partitioned between 10% aqueous hydrochloric acid and ethyl acetate. The ethyl acetate layer was separated, dried over sodium sulphate and concentrated in vacuo to afford a yellow oil.

This oil was dissolved in acetic anhydride(20 ml) containing sodium acetate (0.1 mM) and heated to 90° C. for three hours. The reaction mixture was cooled, poured into water and extracted thrice with ethyl acetate. The ethyl acetate layer was separated, dried over sodium sulphate and concentrated in vacuo to afford a yellow oil. Chromatography over silica gel gave the succinoyl glycine benzyl ester.

10% Palladium on carbon catalyst (5 wt %) was added to a stirred solution of the succinoyl benzyl ester (0.009 M) in methanol (50 ml). Hydrogen gas was bubbled through this solution for three hours. The solution was then filtered over celite and concentrated in vacuo to give the corresponding acid as a white solid.

A solution of the acid (0.1 mM) in dry dichloromethane was cooled to 0° C. and treated with dimethylformamide (0.1 mM) followed by oxalyl chloride (0.1 mM). The cooling bath was removed and the reaction mixture was refluxed for one hour. 4-(piperidyl)aniline (0.1 mM) was then added to the reaction mixture and this solution was stirred for two hours at room temperature. The reaction was then diluted with dichloromethane, washed with saturated aqueous sodium bicarbonate and water. The organic layer was dried over sodium sulphate and concentrated in vacuo. The residue obtained was chromatographed to afford the desired product.

$^1$HNMR: δ 1.5–1.7 (6H, m), 2.8 (4H, s), 3.10 (4H, t), 4.3 (2H, s), 6.85 (2H, d), 7.30 (2H, d), 7.42 (1H, br s)

EXAMPLE 28

2-(2,5-Dioxopyrrolidinyl)-N-(4-piperidylphenyl) propanamide

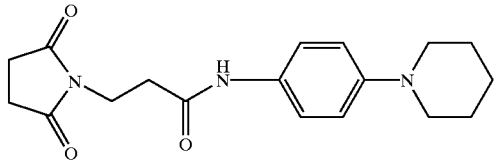

The procedure according to Example 27 was repeated using instead β-alanine benzyl ester hydrochloride.

$^1$HNMR: δ 1.50–1.85 (6H, m), 2.65–2.80 (6H, m), 3.05 (4H, t), 3.9 (2H, t), 6.85 (2H, d), 7.35 (2H, d), 7.4–7.5 (1H, br s)

EXAMPLE 29

3-Ethyl-1-nonylpyrrolidine-2,5-dione

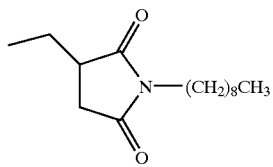

A solution of succinimide (15.15 mM) in tetrahydrofuran (15 ml) containing hexamethyl phosphorus triamide at −78° C. was treated with a solution of lithium diisopropylamide (30.30 mM) in tetrahydrofuran (25 ml). This solution was stirred at −78° C. for one hour and then treated with ethyl iodide (15.90 mM). The reaction mixture was stirred at −78° C. for 30 minutes, warmed up to room temperature and quenched with saturated aqueous ammonium chloride. The organic layer was separated and the aqueous layer extracted with ethyl acetate(3×25 ml). The combined organic layers were washed with 10% aqueous sodium thiosulfate, brine, dried over sodium sulfate and concentrated in vacuo. Chromatography over silica gel afforded pure 3-ethyl succinimide.

A solution of 3-ethyl succinimide (4.72 mM) in dimethylformanide (10 ml) was treated with sodium hydride (5.20 mM) and nonyl bromide (5.20 mM). The reaction mixture was stirred at room temperature for two hours and then quenched with saturated aqueous ammonium chloride. The organic layer was separated and the aqueous layer extracted with ethyl acetate(3×25 ml). The combined organic layers were washed with 10% aqueous sodium thiosulfate, brine, dried over sodium sulfate and concentrated in vacuo. Chromatography over silica gel afforded the desired product, pure 3-ethylN-nonyl succinimide.

$^1$HNMR: δ 0.8 (3H, t), 0.9 (3H, t), 1.15–1.35 (12H, m), 1.45–1.65 (3H, m), 1.80–1.95 (1H, m), 2.35 (1H, dd), 2.6–2.95 (2H, m), 3.45 (2H, dd)

EXAMPLE 30

3-(2-Aminoethylthio)-1-nonylpyrrolidine-2,5-dione

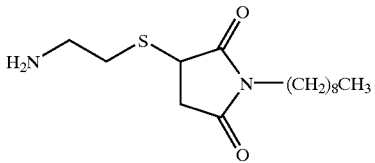

A mixture of N-nonyl maleimide (0.01 M) prepared as described in Example 12 above, mercapto ethylamine (0.01 M) and triethylamine (0.001 M) in acetonitrile (50 ml) was stirred for 24 hours at room temperature. Acetonitrile was evaporated in vacuo and the residue obtained was triturated with ethyl acetate (25 ml). The resultant suspension was filtered and the solid washed with ethyl acetate. The solid was then dried and characterised as the desired product, N-nonyl,3-mercapto ethylamino maleimide.

$^1$HNMR:

δ 0.85 (3H, t), 1.15–1.35 (12H, m), 1.45–1.55 (2H, m), 2.55 (2H, dd), 3.1–3.3 (2H, m), 3.35–3.50 (4H, m), 4.1 (1H, dd), 7.5–7.9 (2H, broads)

EXAMPLE 31

2-Ethyl-N-(2-(1-nonyl-2,5-dioxopyrrolidin-3-ylthio) ethyl)hexanamide

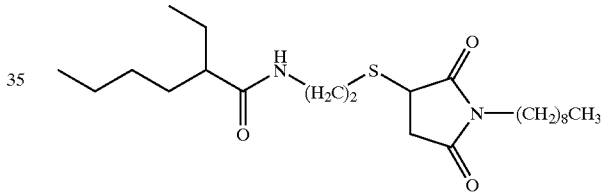

N-nonyl,3-mercapto ethylamino maleimide (0.5 mM) prepared as described in Example 30 above in 2 ml of dichloromethane was treated with one equivalent of triethylamine and one equivalent of 2-ethylhexanoyl chloride. The reaction mixture was stirred for five hours. The dichloromethane was then evaporated to leave a residue to which a saturated sodium bicarbonate solution (2 ml) was added with stirring for 30 minutes, followed by ethyl acetate (2 ml) with stirring for a further 30 minutes. The ethyl acetate layer was then separated and concentrated to yield the desired product.

EXAMPLE 32

Cyclopropyl-N-(2-(2-nonyl-2,5-dioxopyrrolidin-3-ylthio)ethyl)formamide

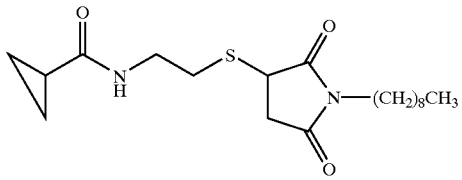

The procedure of Example 31 was repeated using instead cyclopropanecarbonyl chloride.

EXAMPLE 33

(4-Butyliphenyl)-N-(2-(1-nonyl-2,5-dioxopyrrolidin-3-ylthio)ethyl)formamide

The procedure of Example 31 was repeated using instead 4-butylbenzoyl chloride.

EXAMPLE 34

(4-Hexyloxyphenyl)-N-(2-(1-nonyl-2,5-dioxopyrrolidin-3-ylthio)ethyl)formamide

The procedure of Example 31 was repeated using instead 4-hexyloxybenzoyl chloride.

EXAMPLE 35

(4-Methylphenyl)-N-(2(1-nonyl-2,5-dioxopyrrolidin-3-ylthio)ethyl)formamide

The procedure of Example 31 was repeated using instead 4-methylbenzoyl chloride.

EXAMPLE 36

(4-(tert-Butyl)phenyl-N-(2-(1-nonyl-2,5-dioxopyrrolidin-3-ylthio)ethyl)formamide The procedure of Example 31 was repeated using instead 4-tert-butylbenzoyl chloride.

EXAMPLE 37

Cycloventyl-N-(2-(1-nonyl-2,5-dioxopyrrolidin-3-ylthio ethyl)formamide ethane

The procedure of Example 31 was repeated using instead cyclopentanecarbonyl chloride.

EXAMPLE 38

Cyclopentyl-N-(2-nonyl-2,5-diozopyrrolidin-3-ylthio)ethyl)formamide, ethane

The procedure of Example 31 was repeated using instead cyclohextanecarbonyl chloride.

EXAMPLE 39

(4-Nitrophenyt)-N-(2-(1-nonyl-2,5-dioxopyrrolidin-3-ylthio)ethyl)formamide

The procedure of Example 31 was repeated using instead 4-nitrobenzoyl chloride.

EXAMPLE 40

3-((2-(Dibutylamino)ethyl)amino)-1-nonylpyrrolidine-2,5-dione

N-nonyl maleimide (0.02 mM) prepared as described in Example 12 above in 2 ml of acetonitrile was treated with one equivalent of triethylamine and one equivalent of N,N-dibutylethylenediamine. The reaction mixture was stirred for six hours and then the acetonitrile was evaporated. The residue obtained was treated with cold aqueous dilute hydrochloric acid solution and ethyl acetate, with stirring for one hour. The ethyl acetate layer was then separated and concentrated to give the desired product.

EXAMPLE 41

3-((2-(Diethylamino)ethyl)amino)-1-nonylpyrrolidine-2,5-dione

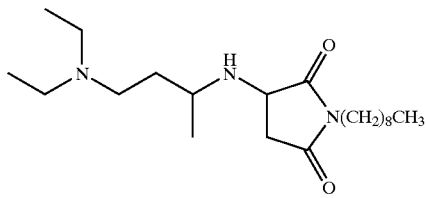

The procedure of Example 40 was repeated using instead 3-diethylamino-1-methylpropylamine.

EXAMPLE 42

1-Nonyl-3-((4-piperidinylphenyl)amino)pyrrolidine-2,5-dione

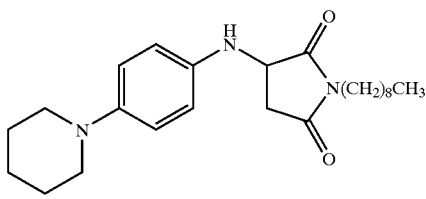

The procedure of Example 40 was repeated using instead 4-(piperidyl)aniline.

EXAMPLE 43

3-(Hydroxyethylthio)-3-methyl-1-nonylpyrrolidine-2,5-dione

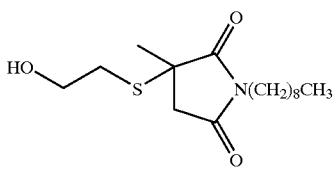

A solution of N-nonyl citraconimide (0.5 mM) prepared as described in Example 5 above in dimethylformamide (10 ml) was treated with triethylamine (0.5 mM) and then 2-mercaptoethanol (0.5 mM) was added dropwise. The progress of the reaction was monitored by thin layer chromatography and when the starting material could no longer be detected the reaction mixture was concentrated in vacuo. The residue obtained was dissolved in ethyl acetate, washed with water and dried over sodium sulfate. Purification by chromatography yielded the desired product.

EXAMPLE 44

3-(2-Aminoethylthio)-3-methyl-1-nonylpyrrolidine-2,5-dione

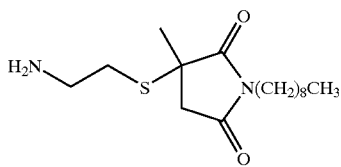

The procedure of Example 43 was repeated using instead 2-mercaptoethylamine.

EXAMPLE 45

3-Methyl-1-octyl-3-(octylaniino)pyrrolidine-2,5-dione.

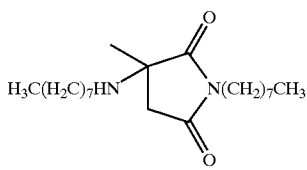

A solution of N-octyl citraconimide (0.223 g, 1 mM) prepared as described in Example 7 above in acetonitrile (2 ml) was treated with triethylamine (0.14 ml, 1 mM) and then octylamine (0.165 ml, 1 mM) was added dropwise. The progress of the reaction was monitored by thin layer chromatography and when the starting material could no longer be detected the reaction mixture was concentrated in vacuo. The residue obtained was dissolved in ethyl acetate, washed with water and dried over sodium sulfate. Purification by chromatography yielded the desired product.

$^1$HNMR: δ 0.8 (6H, t), 1.10–1.28 (20H, m), 1.3 (3H, s), 1.32–1.58 (4H, m), 2.25–2.48 (2H, m), 2.50 & 2.80 (2H, ABq), 3.42 (2H, dd)

EXAMPLE 46

Each of the compounds of Examples 1 to 45 was assessed for bactericidal activity against *M. tuberculosis* by measuring its minimum inhibitory concentration (MIC) in the "BACTEC" (trade mark) system developed by Becton-Dickinson Diagnostic Instrument Systems, Sparks, U.S.A., which is based on a radiometric principle whereby carbon dioxide released by the catabolism of $^{14}$C-palmitate is spectrophotometrically detected and quantitated in arbitrary units of measurement referred to as growth index (GI) units.

Thus, "BACTEC" vials were inoculated with 0.1 ml of *M. tuberculosis* (final bacterial concentration, $1 \times 10^5$ colony forming units per ml) and 0.1 ml of test compound in a range of concentrations. GI values were monitored until a value of ≧30 was achieved for the 1:100 dilution control.

For the purpose of this test, MIC is defined as the minimum concentration of test compound that effects a >95% inhibition of the culture in comparison to the undiluted control, when the control reaches a GI value of 999.

Endpoint determination (>99% inhibition) is based on a conventional 1% resistance cut-off, wherein the organism is considered resistant to a particular concentration of test compound if growth of greater than 1% of the bacterial population is observed. Thus, a comparison is made between growth of the organism in the presence of a pre-determined concentration of test compound and growth of the same organism diluted 1:100 in the absence of any test compound. The change in the GI values (ΔGI) is used to determine the endpoint susceptibility of the organism to the test compound. If the ΔGI of the 1:100 control is greater than the ΔGI in the presence of the test compound, then the concentration of test compound used is considered to be bactericidal (>99% inhibition) for the organism.

The MIC of the compounds of Examples 1 to 46 were determined for the following strains of *M. tuberculosis:*

H37Rv,

H37Ra, 1 clinical isolate susceptible to isoniazid, rifampicin, ethambutol and streptomycin

[E:22/95; Estonia], 1 clinical isolate resistant to isoniazid [H:997/94; Honduras], 1 clinical isolate resistant to isoniazid and ethambutol [E:5/94; Estonia], 1 clinical isolate resistant to isoniazid and rifampicin [H:44/95; Honduras], 1 clinical isolate resistant to isoniazid and streptomycin [S:150/96; Sweden], 1 clinical isolate resistant to isoniazid, rifampicin and streptomycin [AA:063; Ethiopia], 3 clinical isolates resistant to isoniazid, rifampicin, streptomycin and ethambutol [P:24/95; Estonia, S:39/95; Nepal, S:42/95; China, H: 1005/94; Honduras], and were found in all cases to be less than or equal to 20 $\mu$g/ml. Therefore, the compounds of Examples 1 to 46 demonstrate effective bactericidal activity against the above strains of *M. tuberculosis* which include single- and multiple-drug resistant strains.

What is claimed is:

1. A method of treating a patient suffering from, or at risk of, a mycobacterial disease, which comprises administering to the patient a therapeutically effective amount of a compound of formula (I), or a pharmaceutically acceptable salt or solvate thereof, (I)

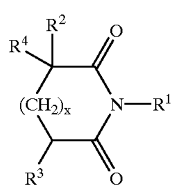

wherein x is 0 or 1;

$R^1$ represents a hydrogen atom, or a $C_1$–$C_{20}$ alkyl or myrtanyl group, or a phenyl or benzyl group optionally substituted in the aromatic ring by one or more substituents selected from amino, nitro, hydroxyl, carboxyl, halogen, trifluoromethyl, $C_1$–$C_6$ alkyl, $C_1$–$C_6$ alkoxy, $C_1$–$C_6$ alkoxycarbonyl, piperidyl, piperazinyl and morpholinyl, or a group $(CH_2)_yCONH$—$R^5$ where y is an integer from 1 to 6 and $R^5$ represents a phenyl group optionally substituted by one or more substituents selected from amino, nitro, hydroxyl, carboxyl, halogen, trifluoromethyl, $C_1$–$C_6$ alkyl, $C_1$–$C_6$ alkoxy, $C_1$–$C_6$ alkoxycarbonyl, piperidyl, piperazinyl and morpholinyl; and either $R^2$ represents a hydrogen atom or a $C_1$–$C_6$ alkyl group, or $R^2$ together with $R^3$ represents a carbon-carbon single bond provided that x is 0, or $R^2$ together with $R^4$ represents a group $=CH_2$, $R^3$ represents a hydrogen atom or is linked to $R^2$ as defined above, and $R^4$ represents a hydrogen atom or a $C_1$–$C_6$ alkyl group; or a $C_1$–$C_{10}$ alkylamino group optionally substituted by a di($C_1$–$C_6$ alkyl)amino substituent group; or an anilino group substituted in the aromatic ring by one or more substituents selected from amino, nitro, hydroxyl, carboxyl, trifluoromethyl, $C_1$–$C_6$ alkyl, $C_1$–$C_6$ alkoxy, $C_1$–$C^6$ alkoxycarbonyl, piperidyl, piperazinyl and morpholinyl; or a group $—SCH_2CH_2OH$, $—SCH_2CH_2NH_2$, $—SCH_2CH_2(NH_2)\ CO_2H$ or $—SCH_2CH_2NHCO—R^6$ where $R^6$ represents a $C_1$–$C_{10}$ alkyl or $C_3$–$C_6$ cycloalkyl group, or a phenyl group optionally substituted by one or more substituents selected from amino, nitro, hydroxyl, carboxyl, halogen, trifluoromethyl, $C_1$–$C_6$ alkyl, $C_1$–$C_6$ alkoxy, $C_1$–$C_6$ alkoxycarbonyl, piperidyl, piperazinyl and morpholinyl;

or $R^4$ is linked to $R^2$ as defined above;

or $R^2$, $R^3$ and $R^4$ together represent a phenyl group;

with the provisos that;

(i) $R^1$, $R^2$, $R^3$ and $R^4$ do not each simultaneously represent a hydrogen atom, and (ii) when x is 0, $R^1$ represents a 4-fluorophenyl group and $R^4$ represents a hydrogen atom, then $R^2$ and $R^3$ do not together represent a carbon-carbon single bond.

2. The method according to claim 1, wherein $R^4$ represents hydrogen atom or a $C_1$–$C_6$ alkyl group; or a $C_1$–$C_{10}$ alkylamino group optionally substituted by a di($C_1$–$C_6$ alkyl)amino substituent group; or a group $—SCH_2CH_2OH$, $—SCH_2CH_2NH_2$, $SCH_2CH_2(NH_2)CO_2H$ or $—SCH_2CH_2NHCO—R^6$ where $R^6$ represents a $C_1$–$C_{10}$ alkyl or $C_3$–$C_6$ cycloalkyl group, or a phenyl group optionally substituted by one or more substituents selected from amino, nitro, hydroxyl, carboxyl, halogen, trifluoromethyl, $C_1$–$C_6$ alkyl, $C_1$–$C_6$ alkoxy, $C_1$–$C_5$ alkoxycarbonyl, piperidyl, piperazinyl and morpholinyl; or $R^4$ is linked to $R^2$ as defined in claim 1.

3. The method according to claim 1, wherein $R^1$ represents a hydrogen atom, or a $C_4$–$C_{10}$ alkyl or myrtanyl group, or a phenyl group substituted by a piperidyl substituent group, or a group $(CH_2)_yCONH$—$R^5$ where y is 1 or 2 and $R^5$ represents a phenyl group substituted by a piperidyl substituent group.

4. The method according to claim 1, wherein $R^2$ represents a hydrogen atom or a methyl group, or $R^2$ together with $R^3$ represents a carbon-carbon single bond provided that x is 0, or $R^2$ together with $R^4$ represents a group $=CH_2$.

5. The method according to claim 1, wherein $R^4$ represents a hydrogen atom, a methyl or ethyl group, a $C_2$–$C_{10}$ alkylamino group optionally substituted by a di($C_2$–$C_4$ alkyl)amino substituent group, an anilino group substituted by a piperidyl substituent group, $—SCH_2CH_2OH$, $—SCH_2CH_2\ (NH_2)CO_2H$, $—SCH_2CH_2NHCO—R^6$ where $R^6$ represents a $C_7$ alkyl, cyclopropyl, cyclopentyl or cyclohexyl group or a phenyl group substituted by a nitro, $C_1$–$C_4$ alkyl or $C_3$–$C_6$ alkoxy substituent group, or $R^4$ is linked to $R^2$ as defined in claim 1.

6. The method according to claim 1, wherein the compound of formula (I) is selected from:

1-Decylpyrrolidine-2,5-dione;

1-Nonylpiperidine-2,6-dione;
2-((6,6-Dimethylbicyclo[3,1,1]hept-2-yl)methyl) isoindole-1,3-dione;
1-((6,6-Dimethylbicyclo[3,1,1]hept-3-yl)methyl)-3-methyl-3-pyrroline-2,5-dione;
3-Methyl-1-nonyl-3-pyrroline-2,5-dione;
3-Methylene-1-nonylpyrrolidine-2,5-dione;
3-Methyl-1-octyl-3-pyrroline-2,5-dione;
3-Methylene-1-octylpyrrolidine-2,5-dione;
(4-(3-methyl-2,5-dioxo-3-pyrrolinyl)phenyl)piperidine;
1-Octyl-3-pyrroline-2,5-dione;
1-Decyl-3-pyrroline-2,5-dione;
1-Nonyl-3-pyrroline-2,5-dione;
1-Butyl-3-pyrroline-2,5-dione;
1-Hexyl-3-pyrroline-2,5-dione;
1-(4-Piperidylphetiyl)-3-pyrroline-2,5-dione;
1-(Octyl-3-(octylamino)-pyrroline-2,5-dione;
1-Decyl-3-(decylamino)pyrrolidine-2,5-dione;
3-(Octylamino)-3-pyrrolidine-2,5-dione;
3-(Heptylamino)-1-nonyl pyrrolidine-2,5-dione;
1-Nonyl-3-(nonylamino) pyrrolidine-2,5-dione;
1-Nonyl-3-(octylamino) pyrrolidine-2,5-dione;
2-Amino-3-(3-methyl-1-nonyl-2,5-dioxo-pyrrolidin-3-ylthio)propanoic acid;
2-Amino-3-(3-methyl-1-octyl-2,5-dioxo-pyrrolidin-3-ylthio)propanoic acid;
2-Amino-3-(1-octyl-2,5-dioxo-pyrrolidin-3-ylthio) propanoic acid;
3-Methyl-1-octylpyrrolidine-2,5-dione;
3-Methyl-1-nonylpyrrolidine-2,5-dione;
2-(2,5-Dioxopyrrolidinyl)-N-(4-piperidylphenyl) ethanamide;
2-(2,5-Dioxopyrrolidinyl)-N-(4-piperidylphenyl) propanamide;
3-Ethyl-1-nonylpyrrolidine-2,5-dione;
3-(2-Aminoethylthio)-1-nonylpyrrolidine-2,5-dione;
2-Ethyl-N-(2-(1-nonyl-2,5-dioxopyrrolidin-3-ylthio) ethyl)hexanamide;
Cyclopropyl-N-(2-(1-nonyl-2,5-dioxopyrrolidin-3-ylthio)ethyl)formamide;
(4-Butylphenyl)-N-(2-(1-nonyl-2,5-dioxopyrrolidin-3-ylthio)ethyl)formamide;
(4-Hexyloxyphenyl)-N-(2-(1-nonyl-2,5-dioxopyrrolidin-3-ylthio)ethyl)formamide;
(4-Methylphenyl)-N-(2-(1-nonyl-2,5-dioxopyrrolidin-3-ylthio)ethyl)formamide;
(4-(tert-Butyl)phenyl-N-(2-(1-nonyl-2,5-dioxopyrrolidin-3-ylthio)ethyl)formamide;
Cyclopentyl-N-(2-(1-nonyl-2,5-dioxopyrrolidin-3-ylthio) ethyl)formamide;
Cyclohexyl-N-(2-(1-nonyl-2,5-dioxopyrrolidin-3-ylthio) ethyl)formamide;
(4-Nitrophenyl)-N-(2-(1-nonyl-2,5-dioxopyrrolidin-3-ylthio)ethyl)formamide;
3-((2-(Dibutylamino)ethyl)amino)-1-nonylpyrrolidine-2,5-dione;
3-((2-(Diethylamino)ethyl)amino)-1-nonylpyrrolidine-2,5-dione;
1-Nonyl-3-((4-piperidinylphenyl)amino)pyrrolidine-2,5-dione;
3-(Hydroxyethylthio)-3-methyl-1-nonylpyrrolidine-2,5-dione;
3-(2-Aminoethylthio)-3-methyl-1-nonylpyrrolidine-2,5-dione; and
3-Methyl-1-octyl-3-(octylamino)pyrrolidine-2,5-dione.

7. The method according to any one of claims 1–6, wherein the mycobacterial disease is tuberculosis.

\* \* \* \* \*

UNITED STATES PATENT AND TRADEMARK OFFICE
CERTIFICATE OF CORRECTION

PATENT NO.     : 6,476,053 B1
DATED          : November 5, 2002
INVENTOR(S)    : Balganesh et al.

It is certified that error appears in the above-identified patent and that said Letters Patent is hereby corrected as shown below:

Column 22,
Line 11, replace "$C_1$–$C^6$" with -- $C_1$–$C_6$ --.
Line 41, replace "$C_1$–$C_5$" with -- $C_1$–$C_6$ --.

Column 23,
Line 18, replace "Piperidylphetiyl" with -- Piperidylphenyl --.

Signed and Sealed this

Seventeenth Day of June, 2003

JAMES E. ROGAN
*Director of the United States Patent and Trademark Office*